US010918321B2

(12) United States Patent
Benni

(10) Patent No.: US 10,918,321 B2
(45) Date of Patent: *Feb. 16, 2021

(54) METHOD FOR SPECTROPHOTOMETRIC BLOOD OXYGENATION MONITORING

(71) Applicant: Edwards Lifesciences Corporation, Irvine, CA (US)

(72) Inventor: Paul B. Benni, Acton, MA (US)

(73) Assignee: Edwards Lifesciences Corporation, Irvine, CA (US)

( * ) Notice: Subject to any disclaimer, the term of this patent is extended or adjusted under 35 U.S.C. 154(b) by 480 days.

This patent is subject to a terminal disclaimer.

(21) Appl. No.: 15/845,503

(22) Filed: Dec. 18, 2017

(65) Prior Publication Data

US 2018/0192928 A1  Jul. 12, 2018

Related U.S. Application Data

(63) Continuation of application No. 14/335,458, filed on Jul. 18, 2014, now Pat. No. 9,848,808.

(Continued)

(51) Int. Cl.
*A61B 5/1455* (2006.01)
*A61B 5/00* (2006.01)

(52) U.S. Cl.
CPC .......... *A61B 5/14552* (2013.01); *A61B 5/72* (2013.01); *A61B 5/6814* (2013.01); *A61B 5/6833* (2013.01)

(58) Field of Classification Search
CPC . A61B 5/0205; A61B 5/1455; A61B 5/14551; A61B 5/14552; A61B 5/72;

(Continued)

(56) References Cited

U.S. PATENT DOCUMENTS 3,638,640 A   2/1972   Shaw
4,281,645 A   8/1981   Jobsis
(Continued)

FOREIGN PATENT DOCUMENTS

WO   WO0184107 A2   11/2001
WO   WO2004010844 A2   2/2004

OTHER PUBLICATIONS

Benni et al. "A Novel Near-Infrared Spectroscopy (NIRS) System for Measuring Regional Oxygen Saturation", Department of Anesthesia, Robert Wood Johnson Medical School, May 22, 1995.

(Continued)

*Primary Examiner* — Chu Chuan Liu
(74) *Attorney, Agent, or Firm* — Getz Balich LLC

(57) ABSTRACT

An apparatus and method for non-invasively determining a blood oxygen parameter value of a subject's tissue is provided. An embodiment of the method includes the steps of: a) providing a spectrophotometric sensor that includes a processing portion and a transducer, b) detecting at least a portion of transmitted light after passage through the subject's tissue and producing initial signal data from the detected light; and c) using the processing portion to: (i) determine a value representative of an attenuation of at least one wavelength of light detected; (ii) determine whether the representative attenuation value is outside a predefined range of attenuation values; and (iii) determine the blood oxygen parameter value using a first interrogation or an alternate interrogation setting.

14 Claims, 7 Drawing Sheets

Related U.S. Application Data

(60) Provisional application No. 61/847,855, filed on Jul. 18, 2013.

(58) Field of Classification Search
CPC ... A61B 5/6833; A61B 5/6814; A61B 5/7221; A61B 5/7271; A61B 5/68; A61B 5/6801; A61B 5/6802; A61B 5/6803; A61B 5/6813
See application file for complete search history.

(56) References Cited

U.S. PATENT DOCUMENTS

| | | | |
|---|---|---|---|
| 4,570,638 A | 2/1986 | Stoddart et al. | |
| 4,714,341 A | 12/1987 | Hamaguri et al. | |
| 4,725,147 A | 2/1988 | Stoddart | |
| 4,768,516 A | 9/1988 | Stoddart et al. | |
| 4,805,623 A | 2/1989 | Jobsis | |
| 4,817,623 A | 4/1989 | Stoddart et al. | |
| 4,907,876 A | 3/1990 | Suzuki et al. | |
| 5,040,539 A | 8/1991 | Schmitt et al. | |
| 5,054,488 A | 10/1991 | Muz | |
| 5,139,025 A | 8/1992 | Lewis et al. | |
| 5,153,669 A | 10/1992 | DeGroot | |
| 5,218,962 A | 6/1993 | Mannheimer et al. | |
| 5,246,002 A | 9/1993 | Prosser | |
| 5,251,632 A | 10/1993 | Delpy | |
| 5,299,579 A | 4/1994 | Gedeon et al. | |
| 5,348,004 A | 9/1994 | Hollub | |
| 5,349,961 A | 9/1994 | Stoddart et al. | |
| 5,413,100 A | 5/1995 | Barthelemy et al. | |
| 5,421,329 A | 6/1995 | Casciani et al. | |
| 5,482,034 A | 1/1996 | Lewis et al. | |
| 5,517,987 A | 5/1996 | Tsuchiya | |
| 5,524,617 A | 6/1996 | Mannheimer | |
| 5,529,065 A | 6/1996 | Tsuchiya | |
| 5,632,273 A | 5/1997 | Suzuki | |
| 5,676,142 A | 10/1997 | Miwa et al. | |
| 5,706,821 A | 1/1998 | Matcher et al. | |
| 5,770,454 A | 6/1998 | Essenpreis et al. | |
| 5,772,589 A | 6/1998 | Bernreuter | |
| 5,782,756 A | 7/1998 | Mannheimer | |
| 5,803,909 A | 9/1998 | Maki et al. | |
| 5,853,370 A | 12/1998 | Chance et al. | |
| 5,902,235 A | 5/1999 | Lewis et al. | |
| 6,192,260 B1 | 2/2001 | Chance | |
| 6,456,862 B2 | 9/2002 | Benni | |
| 6,512,936 B1 | 1/2003 | Monfre et al. | |
| 6,516,209 B2 | 2/2003 | Cheng et al. | |
| 6,615,065 B1 | 9/2003 | Barrett et al. | |
| 6,882,874 B2 | 4/2005 | Huiku | |
| 7,029,444 B2 | 4/2006 | Shin et al. | |
| 7,072,701 B2 | 7/2006 | Chen et al. | |
| 8,116,837 B2 * | 2/2012 | Huang | A61B 5/14551 600/310 |
| 9,560,994 B2 * | 2/2017 | McCutcheon | A61B 5/14551 |
| 9,839,381 B1 * | 12/2017 | Weber | A61B 5/0059 |
| 2008/0017800 A1 | 1/2008 | Benni | |
| 2009/0163819 A1 | 6/2009 | De Kok et al. | |
| 2009/0281403 A1 | 11/2009 | Benni | |
| 2012/0071739 A1 | 3/2012 | Chen et al. | |

OTHER PUBLICATIONS

Jacques et al. "The Melanosome: Threshold Temperature for Vaporization and Internal Absorption Coefficient During Pulsed Laser Irradiation", Photochemistry and Photobiology, vol. 53, No. 6, pp. 769-775, 1991.

"Pulse Oximetry", NanoViova LLC, 2012, Web. Jan. 11, 2017. https://sites.google.com/a/nanoviova.com/www1/technology-expertise/pulse-oximetry.

* cited by examiner

Biliverdin Absorption Spectrum

METHOD FOR SPECTROPHOTOMETRIC BLOOD OXYGENATION MONITORING

This application is a continuation of U.S. patent application Ser. No. 14/335,458 filed Jul. 18, 2014, which claims priority to U.S. Patent Appln. No. 61/847,855 filed Jul. 18, 2013.

This invention was made with Government support under Contract No. NS045488 awarded by the National Institutes of Health. The Government has certain rights in the invention.

BACKGROUND OF THE INVENTION

1. Technical Field

This invention relates to methods for non-invasively determining biological tissue oxygenation in general, and to non-invasive methods utilizing near-infrared spectroscopy (NIRS) techniques for determining the same in particular.

2. Background Information

U.S. Pat. Nos. 6,456,862; 7,072,701; and 8,396,526, all assigned to the assignee of the present application and all hereby incorporated by reference, disclose methods for spectrophotometric blood oxygenation monitoring. Oxygen saturation within blood is defined as:

$$O_2 \text{ saturation \%} = \frac{HbO_2}{(HbO_2 + Hb)} * 100\% \quad \text{(Eqn. 1)}$$

These methods, and others known within the prior art, utilize variants of the Beer-Lambert law to account for optical attenuation in tissue at a particular wavelength. The term "absorb" in various different forms is often used to refer to light attenuation. Numerous physical phenomena may collectively cause light attenuation, including light scattering and absorptive phenomena. Relative concentrations of oxyhemoglobin ($HbO_2$) and deoxyhemoglobin (Hb), and therefore oxygenation levels, within a tissue sample are determinable using changes in optical attenuation:

$$A_\lambda = -\log\left(\frac{I}{I_o}\right)_\lambda = \alpha_\lambda * C * d \quad \text{(Eqn. 2)}$$

wherein "$A_\lambda$" represents the optical attenuation in tissue at a particular wavelength $\lambda$ (units: optical density or OD); "$I_o$" represents the light intensity of the incident light at the wavelength (units: $W/cm^2$); "I" represents the light intensity of the detected light at the wavelength (units: $W/cm^2$); "$\alpha_\lambda$" represents the wavelength dependent absorption coefficient of the chromophore (units: $OD*cm^{-1}*\mu M^{-1}$); "C" represents the concentration of chromophore (units: $\mu M$); and "d" represents the light source to detector (optode) separation distance (units: cm).

To non-invasively determine oxygen saturation within tissue accurately, it is necessary to account for the optical properties (e.g., absorption coefficients or optical densities) of the tissue being interrogated. In some instances, the absorption coefficients or optical densities for the tissue components that create background light absorption and scattering can be assumed to be relatively constant over a selected wavelength range. The graph shown in FIG. 1, which includes tissue data plotted relative to a Y-axis of values representative of absorption coefficient values and an X-axis of NIRS light wavelength values, illustrates such an instance. The aforesaid constant value assumption is reasonable in a test population where all of the subjects have approximately the same tissue optical properties; e.g., skin pigmentation, muscle and bone density, etc. A tissue interrogation method that relies upon such an assumption may be described as being subject independent. Our findings indicate that the same assumption is not reasonable, however, in a population of subjects having a wide spectrum of tissue optical properties.

The validity of an assumption of the tissue and bone characteristics of a test population can also be questioned in instances where the tissue optical properties of tissue or bone is abnormal. One or more of disease, trauma head injury, medication, and an abnormal anatomy can cause abnormal brain and extracerebral components (scalp & skull) tissue optical properties. The abnormality of these properties can be such that conventional tissue oximetry techniques become inaccurate and difficult, and in some cases tissue oximetry algorithms cannot make a calculation at all; e.g., when the optical properties of the altered tissue (including bone) falls out of the expected range.

Examples of disease, injury, or abnormal anatomy that could result in altered tissues (e.g., cerebral and extracerebral tissue) include, but are not limited to, bruises, contusion, scarring, skull fracture, concussion, surgery scarring, sinus infections and other infections, tissue discoloration, bone discoloration, dura pigmentation, bone marrow, forehead hair follicles, etc. These conditions may be natural, or may be the result of injury or medication.

A bruise, also called a contusion, is a type of relatively minor hematoma of tissue in which capillaries and sometimes venules are damaged by trauma, allowing blood to seep into the surrounding interstitial tissues. Bruises can involve capillaries at the level of skin, subcutaneous tissue, muscle, or bone.

As a type of hematoma, a bruise is always caused by internal bleeding into the interstitial tissues, usually initiated by blunt trauma, which causes damage through physical compression and deceleration forces. Trauma sufficient to cause bruising can occur from a wide variety of situations including accidents, falls, and surgeries. Disease states such as insufficient or malfunctioning platelets, other coagulation deficiencies, or vascular disorders, such as venous blockage associated with severe allergies can lead to the formation of bruises in situations in which they would not normally occur and with only minimal trauma. If the trauma is sufficient to break the skin and allow blood to escape the interstitial tissues, the injury is not a bruise but instead a different variety of hemorrhage called bleeding, although such injuries may be accompanied by bruising elsewhere.

Increased distress to tissue causes capillaries to break under the skin, allowing blood to escape and build up. As time progresses, blood seeps into the surrounding tissues, causing the bruise to darken and spread. Nerve endings within the affected tissue detect the increased pressure, which, depending on severity and location, may be perceived as pain or pressure or be asymptomatic. The damaged endothelium (lining) of the affected capillaries releases endothelin, a hormone that causes narrowing of the blood vessel to minimize bleeding. As the endothelium is destroyed, the underlying von Willebrand factor is exposed and initiates coagulation, which creates a temporary clot to plug the wound and eventually leads to restoration of normal tissue.

During this time, larger bruises may change color due to the breakdown of hemoglobin from within escaped red blood cells in the extracellular space. The striking colors of a bruise are caused by the phagocytosis and sequential degradation of hemoglobin to biliverdin to bilirubin to hemosiderin, with hemoglobin itself producing a red-blue color, biliverdin producing a green color, bilirubin producing a yellow color, and hemosiderin producing a golden-brown color. As these products are cleared from the area, the bruise disappears. Often the underlying tissue damage has been repaired long before this process is complete. Therefore during a bruise, hemoglobin breaks down to biliverdin, then to bilirubin, to hemosiderin, which material alters the optical properties of the affected tissue. The hemoglobin breakdown to biliverdin is particularly interesting because the light absorption spectra of biliverdin shows profound light absorption as the wavelength decreases from 900 nm in the near-infrared range down to 600 nm in the red range, similar to the subject data shown in the figures of this application; e.g., See FIG. 2.

The human forehead has more hair follicles (called vellus hair) than any other part of the human body. Because most of vellus hair is fine and pale, it usually is not visible to the naked eye. The thicker, fully pigmented hair most people consider "real hair" is called terminal hair. Terminal hair is found on scalp, eyebrows, legs, backs, underarms. For most people under examination by cerebral oximetry sensor placed on the forehead, the forehead hair follicles have no effect. However for some people, the forehead hair follicle may have excessive pigmentation or other characteristics that can alter the tissue optical properties to a degree where a cerebral oximetry sensor may give an erroneous reading.

As a result of one or more of the aforementioned conditions, the optical characteristics as measured by a reflectance spectroscopy sensor, may show profound differences in the light absorption as the wavelength decreases from 900 nm in the near-infrared range down to 600 nm in the red range compared to normal subjects.

DISCLOSURE OF THE INVENTION

According to an aspect of the present disclosure, a method for non-invasively determining a blood oxygen parameter value of a subject's tissue is provided. The method includes the steps of: a) providing a spectrophotometric sensor that includes a processing portion and a transducer, which transducer is operable to transmit light at predetermined wavelengths into the subject's tissue, and to sense the transmitted light; b) detecting at least a portion of the transmitted light after passage through the subject's tissue using the transducer, and producing initial signal data from the light sensed; and c) using the processing portion to: (i) determine a value representative of an attenuation of at least one of the predetermined wavelengths of light detected using the initial signal data; (ii) determine whether the representative attenuation value is outside a predefined range of attenuation values; and (iii) determine the blood oxygen parameter value using a first interrogation setting if the representative attenuation value is outside the predefined range of attenuation values, or using a second interrogation setting if the representative attenuation value is within the predefined range of attenuation values.

According to another aspect of the present disclosure, a method for non-invasively determining a blood oxygen parameter value of a subject's tissue is provided. The method includes the steps of: a) providing a spectrophotometric sensor that includes a processing portion and a transducer, which transducer is operable to transmit light at predetermined wavelengths into the subject's tissue, and to sense the transmitted light; b) detecting at least a portion of the transmitted light after passage through the subject's tissue using the transducer, and producing initial signal data from the light sensed; and c) using the processing portion to: (i) determine a value representative of an attenuation of at least one of the predetermined wavelengths of light detected using the initial signal data; (ii) determine a value representative of a hemoglobin concentration within the tissue; (iii) determine whether the representative attenuation value is outside a predefined range of attenuation values associated with the determined hemoglobin concentration; and (iv) determine the blood oxygen parameter value using a first interrogation setting if the representative attenuation value is outside the predefined range of attenuation values associated with the determined hemoglobin concentration, or using a second interrogation setting if the representative attenuation value is within the predefined range of attenuation values associated with the determined hemoglobin concentration.

According to another aspect of the present disclosure, a method for non-invasively determining an oxygen saturation value of a subject's tissue is provided. The method includes the steps of: a) providing a spectrophotometric sensor that includes a processing portion and a transducer, which transducer is operable to transmit light at predetermined wavelengths into the subject's tissue, and to sense the transmitted light; b) detecting at least a portion of the transmitted light after passage through the subject's tissue using the transducer, and producing initial signal data from the light sensed; and c) using the processing portion to: (i) determine a value representative of an attenuation of at least one of the predetermined wavelengths of light detected using the initial signal data; (ii) determine a value representative of the oxygen saturation value of the tissue using the initial signal data; (iii) determine whether the representative attenuation value is outside a predetermined range of attenuation values associated with the determined oxygen saturation value; and (iv) determine the blood oxygen parameter value using a first interrogation setting if the representative attenuation value is outside the predefined range of attenuation values associated with the determined oxygen saturation value, or using a second interrogation setting if the representative attenuation value is within the predefined range of attenuation values associated with the determined oxygen saturation value.

According to another aspect of the present invention, a method for non-invasively determining a blood oxygen parameter value of a subject's tissue is provided. The method includes the steps of: a) providing a spectrophotometric sensor that includes a processing portion and a transducer, which transducer is operable to transmit light at predetermined wavelengths into the subject's tissue, and to sense the transmitted light; b) detecting at least a portion of the transmitted light after passage through the subject's tissue using the transducer, and producing initial signal data from the light sensed; and c) using the processing portion to: (i) determine a value representative of attenuation for each of a plurality of the predetermined wavelengths of light detected using the initial signal data; (ii) compare at least one of the representative attenuation values relative to one or more of the other representative attenuation values to determine whether the representative attenuation value for any wavelength is disproportionate to the representative attenuation value of one or more of the other wavelengths; and (iii) determine the blood oxygen parameter value using a first interrogation setting if the representative attenuation value of one or more of the wavelengths is disproportionate to the representative attenuation value of another of the predetermined wavelengths.

According to another aspect of the present disclosure, an apparatus for non-invasively determining a blood oxygen parameter value of a subject's tissue is provided. The apparatus includes a spectrophotometric sensor that includes a processing portion and at least one transducer. The transducer is operable to: a) transmit light at predetermined wavelengths into the subject's tissue; b) detect at least a portion of the transmitted light after passage through the subject's tissue using the transducer; and c) produce initial signal data from the detected light. The processing portion is adapted to: a) determine a value representative of an attenuation of at least one of the predetermined wavelengths of light detected using the initial signal data; b) to determine whether the representative attenuation value is greater than a predefined range of attenuation values; and c) determine the blood oxygen parameter value using a first interrogation setting if the representative attenuation value is outside the predefined range of attenuation values, or using a second interrogation setting if the representative attenuation value is within the predefined range of attenuation values.

These and other objects, features, and advantages of the present invention method and apparatus will become apparent in light of the detailed description of the invention provided below and the accompanying drawings. The methodology and apparatus described below constitute a preferred embodiment of the underlying invention and do not, therefore, constitute all aspects of the invention that will or may become apparent by one of skill in the art after consideration of the invention disclosed overall herein.

DETAILED DESCRIPTION THE INVENTION

The present method for non-invasively determining the blood oxygen saturation level within a subject's tissue is provided that utilizes a near infrared spectrophotometric (NIRS) sensing device 8 (sometimes referred to as an "oximeter") that includes one or more transducers 10 and a processing portion 12. Each transducer 10 is capable of transmitting light signals into the tissue of a subject and sensing the transmitted light signals once they have passed through the tissue via transmittance or reflectance. A variety of NIRS sensing device types can be adapted according to aspects of the present disclosure, and aspects of the present disclosure are not therefore limited to any particular type of NIRS sensing device.

Figure 4:
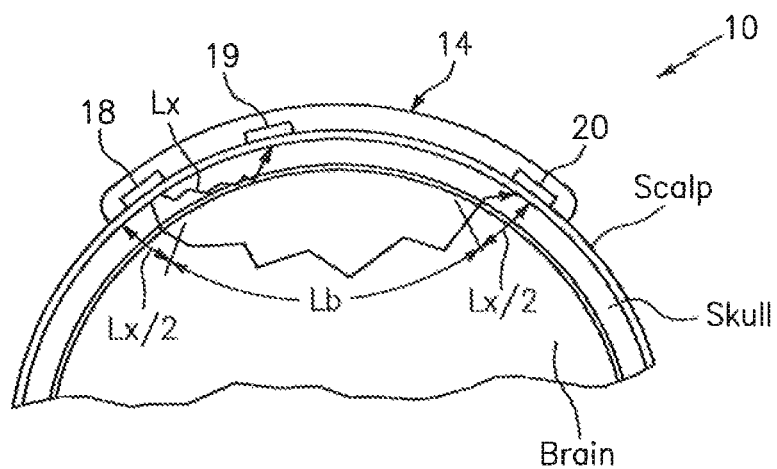
FIG. 4 is a diagrammatic representation of a NIRS sensor.
Figure 5:
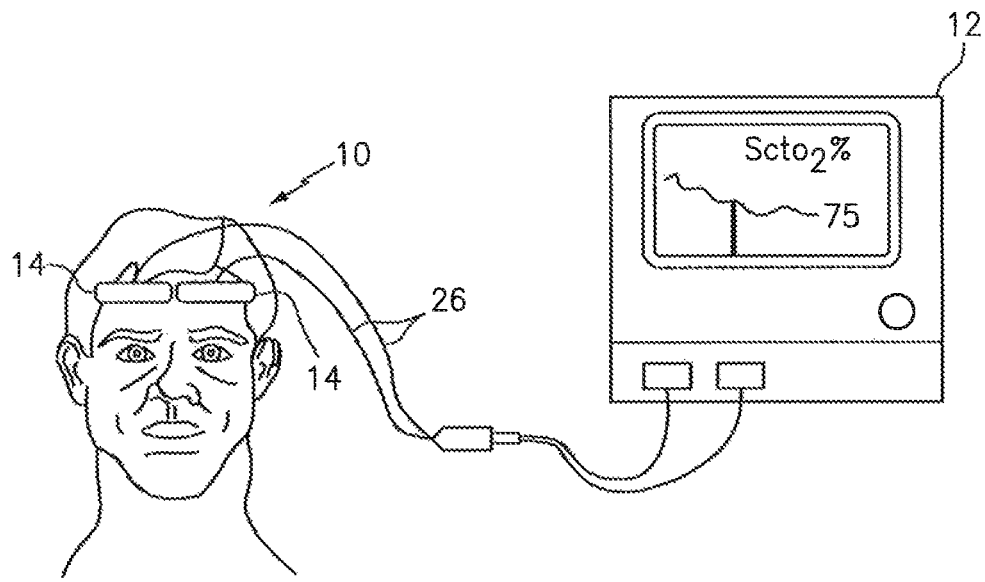
FIG. 5 is a diagrammatic representation of a NIRS sensor placed on a subject's head.
Figure 6:
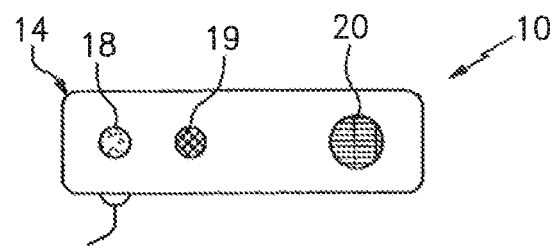
FIG. 6 is a diagrammatic view of a NIRS sensor.

Referring to FIGS. 4-6, an example of an acceptable NIRS sensing device transducer 10 is shown. The transducer 10, which includes a flexible portion that can be attached directly to a subject's body, includes one or more light sources 18 and light detectors 19, 20 mounted within a housing 14. The light detectors 19, 20, may be described as a "near" detector 19 and a "far" detector 20, where the terms "near" and "far" indicate the relative distances from the light source 18. A disposable adhesive envelope or pad may be used to mount the housing 14 easily and securely to the subject's skin. The light sources 18 may be light emitting diodes ("LEDs") that emit light at a narrow spectral bandwidth at predetermined wavelengths. The light sources 18 are not, however, limited to LEDs. A connector cable 26 connects the housing 14 directly or indirectly to the processor portion 12. The light detectors 19, 20 each include one or more photodiodes, or other light detecting devices. The photodiodes are also operably connected to the processor portion 12 via the connector cable 26. Non-limiting examples of acceptable NIRS sensors are described in U.S. Patent Publication No. 2014/0171761 and U.S. Pat. No. 8,428,674, both of which are commonly assigned to the assignee of the present application and both of which are hereby incorporated by reference in their entirety.

The processing portion 12 includes a processor that can be used to control the operations described in association with any of the computer-implemented methods described herein. The processing portion 12 may further include a memory and one or both of a storage device and an input/output device. Each of the components may be interconnected using a system bus. The processor is capable of processing instructions stored in the memory or on the storage device, and to create an information display (e.g., graphical information). The memory can include volatile memory and/or non-volatile memory, and may be a computer readable medium. In general, the storage device can include any non-transitory tangible media configured to store computer readable instructions. In one embodiment, the storage device is a computer-readable medium. The input/output device provides input/output operations for the device. In some embodiments, the input/output device may include a keyboard, a pointing device, a touch screen, or the like. In some embodiments, the input/output device includes a display unit for displaying graphical user interfaces. The features described can be implemented in digital electronic circuitry, or in computer hardware, firmware, or in combinations of them. The features can be implemented in a computer program product tangibly embodied in an information carrier, e.g., in a machine-readable storage device, for execution by a programmable processor; and features can be performed by a programmable processor executing a program of instructions to perform functions of the described embodiments by operating on input data and generating output. The processor is adapted to control operation of the light sources 18 and process light signals provided directly or indirectly from the light detectors 19, 20 as described herein. A person of skill in the art will recognize that the processor may assume various forms (e.g., digital signal processor, analog device, etc.) capable of performing the functions described herein.

Aspects of the present disclosure are operable to non-invasively determine the blood oxygen parameter values; e.g., oxygen saturation values, hemoglobin concentration values, etc. In particular, aspects of the present disclosure are operable to determine the aforesaid information in subjects having tissue optical properties associated with excessive absorption of light at certain wavelengths within the range of wavelengths typically used in NIRS interrogation (e.g., about 600 nm to about 900 nm). Tissue optical properties associated with excessive absorption of light are not "normally" found within the tissue of subjects subjected to NIRS testing under typical NIRS testing conditions. The term "normal" as used herein to describe a subject or a subject's tissue is used to refer to the fact that most people have tissue optical properties within a certain range of values, but a small percentage of people have one or more tissue optical properties with a value outside of the aforesaid range of values. For purposes of the present disclosure, we do not refer to a type of tissue optical properties (there are many including scattering and absorptive phenomena), but rather refer to the tissue optical properties collectively in the context of the absorbance of light traveling within the tissue. The term "normal" as used herein with respect to a subject or a subject's tissue has no necessary relation to the subject's health. Indeed, a subject having "normal" tissue optical properties may be healthy or unhealthy, and conversely a subject having tissue optical properties associated with excessive absorption may be healthy or unhealthy. In short, our experience to date indicates that a substantial majority of subjects whose tissue was interrogated with light at wavelengths used for NIRS interrogation have attenuation values in a predictable range, but a small percentage of subjects whose tissue was interrogated with light at wavelengths used for NIRS interrogation have attenuation values outside that predictable range. For purposes of describing the present disclosure, we refer to tissue interrogated with light at wavelengths used for NIRS interrogation that produce attenuation values outside that predictable range as tissue that "excessively absorbed" or that exhibits "excessive absorption" regardless of the mechanism for the excessive loss (e.g., dispersive or absorptive). Specific absorbance values for the "predictable range" will vary depending upon the parameters used to gather the absorbance values, how the absorbance values are presented (e.g., normalized or not), etc., and therefore the present disclosure is not tied to a particular value range. As indicated above in the Background Information section, our experience is that excessively absorbing tissue may be more often present when certain types of conditions. The existence of these conditions does not, however, guarantee that excessively absorbing tissue will be present. The effect of these tissue optical properties (that excessively absorb certain wavelengths of light) can cause, unless accounted for, erroneous blood oxygen parameter readings; i.e., erroneous oxygen saturation values. The present processing portion 12 is adapted (e.g., by algorithm according to the present method) to account for these tissue optical properties and thereby provide accurate blood oxygen parameter values in those instances.

The processing portion 12 is adapted to determine blood oxygen parameter values, including oxygen saturation values (that may be referred to as "SnO$_2$", "StO$_2$", "SctO$_2$", "CrSO$_2$", "rSO$_2$", etc.) and hemoglobin concentration values (e.g., oxyhemoglobin (HbO2) and/or deoxyhemoglobin (Hb)). As indicated above, U.S. Pat. Nos. 6,456,862; 7,072,701; and 8,396,526 disclose methods for spectrophotometric blood oxygenation monitoring. The methods of determining blood oxygen parameters disclosed in U.S. Pat. Nos. 6,456,862 and 7,072,701 represent acceptable examples of determining a subject-independent blood oxygen parameter value. Aspects of the present disclosure may include, but are not limited to including, those specific methods. The method disclosed in U.S. Pat. No. 8,396,526 represents an acceptable example of a method of determining a blood oxygen parameter value that accounts for the specific physical characteristics of the particular subject's tissue being sensed; i.e., a method that builds upon a subject-independent algorithm such as those disclosed in U.S. Pat. Nos. 6,456,862 and 7,072,701 to make it subject-dependent. Aspects of the present disclosure may include, but are not limited to, the specific methods described in U.S. Pat. No. 8,396,526. The present disclosure described herein provides methods and techniques for modifying such methods for providing accurate determination of blood oxygen parameters for subjects having tissue with optical properties that excessively absorb certain wavelengths of light.

Aspects of the present disclosure improve the accuracy of measuring tissue oxygen saturation (e.g., cerebral oximetry or other NIRS type monitors), by compensating for tissue optical properties that may be independent of skin pigmentation. As indicated above, disease, injury, medication, abnormal anatomy, etc., may cause a subject's tissue (including bone) to have optical properties that excessively absorb certain wavelengths of light. These tissue optical properties can make it difficult or impossible for conventional NIRS tissue oximeters to produce accurate data.

Figure 1:
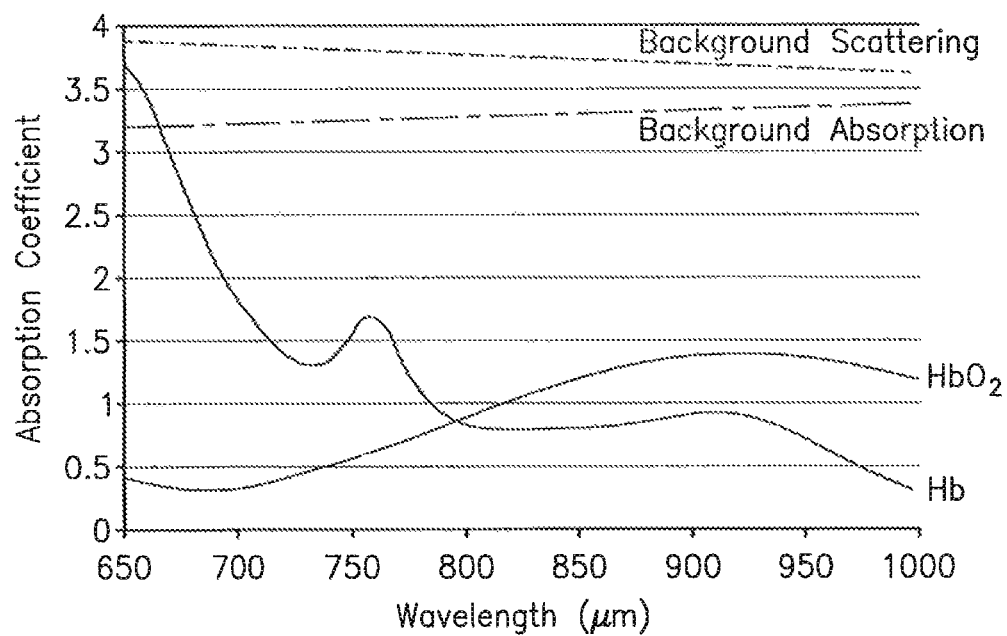
FIG. 1 is a graph diagrammatically illustrating tissue and hemoglobin data plotted relative to a Y-axis of values representative of absorption coefficient values, and an X-axis of wavelength values.
Figure 2:
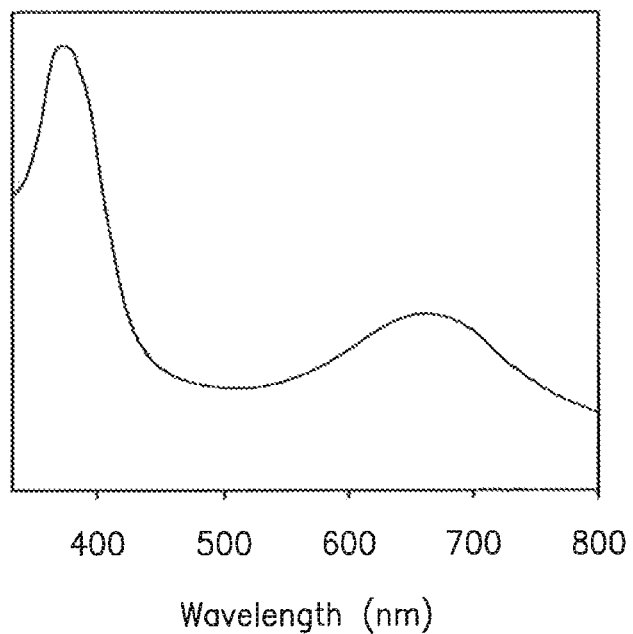
FIG. 2 is a graph depicting Biliverdin absorption spectrum.
Figure 3:
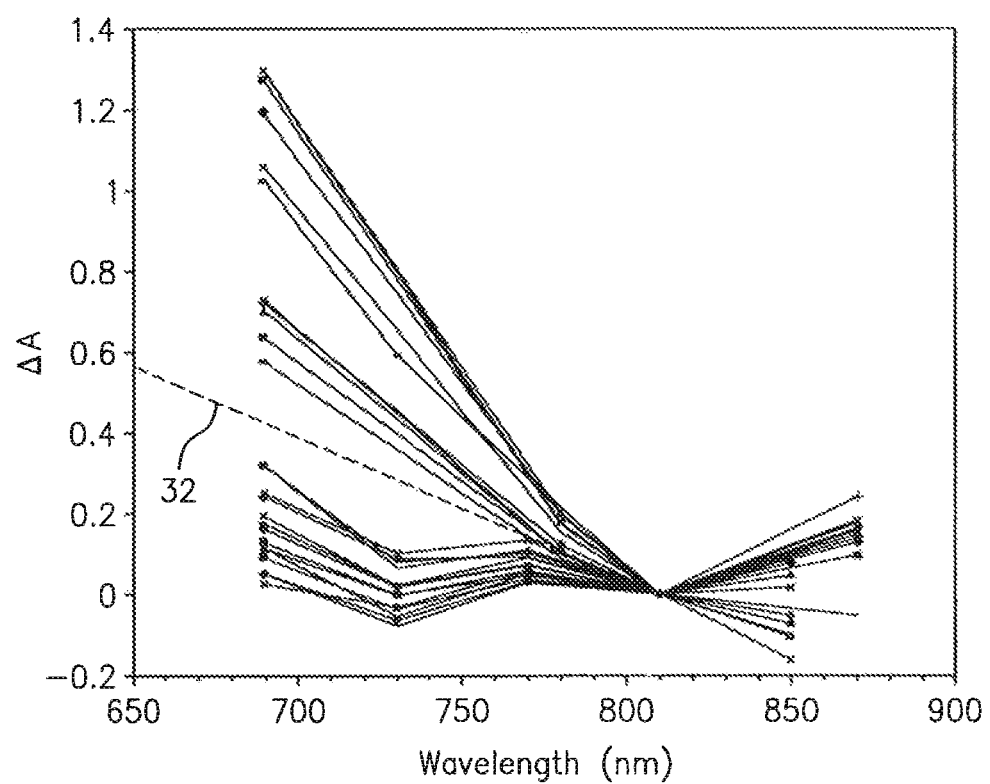
FIG. 3 is a graph illustrating a difference in attenuation versus wavelength, including data attributable to tissue exhibiting excessive absorption.

FIG. 3 illustrates absorption spectra collected from sensing forehead tissue of normal control subjects (i.e., subjects possessing attenuation values in a predictable range for the given test/data format parameters) and also absorption spectra collected sensing forehead tissue of subjects exhibiting excessive absorption of light at certain wavelengths used in NIRS interrogation. All of the subjects used to produce the data depicted in FIG. 3 were healthy subjects having assumed tissue oxygen saturation values that may be considered normal (e.g., StO2 values in the range of 65-80%—as may be determined using Equation 1), breathing room air. The StO2 values of the subjects that exhibited excessive absorption were lower and erroneous, often to the lowest recordable value of 0%. The subjects having tissue that exhibited excessive absorption did not have any blood component that exhibited different optical properties than the control subjects as demonstrated by the fact that when the NIRS sensor was moved onto the subject's calf muscle, normal and expected muscle tissue oxygen saturation measurements were observed. Consequently, the differences in absorption at the different wavelengths at the forehead interrogation position are understood to be attributable to tissue optical properties of the sensed forehead tissue rather than differences in oxygen saturation values. Many of the subjects that produced data indicative of excessive absorption reported a prior history of sinus infections, forehead concussions, sinus cavity surgery, deviated septum, bruising, etc., all of which factors could potentially alter the tissue optical properties of the cerebral and extra-cerebral tissues in the forehead region.

The data shown in FIG. 3 was collected using a Fore-Sight® NIRS oximeter (CAS Medical, Branford Conn.) with a Fore-Sight® sensor (i.e., transducer) placed on the subject's forehead. The Fore-Sight® sensor used for the testing has a light source, a near light detector, and a far light detector. The near light detector is located closer to the light source than the far detector. The sensor configuration used to collect the data shown in FIG. 3 had a near detector located fifteen millimeters (15 mm) from the light source and a far detector located fifty millimeters (50 mm) away from the light source. The spacing of this sensor configuration is advantageous because it allows deeper tissue optical absorption characteristics to be examined by subtracting the superficial tissue interrogated by the near detector from the deep tissue interrogated by the far detector. The present invention is not limited to this particular sensor configuration, however. During the sensing, data was collected at four wavelengths (e.g., 690, 780, 810, and 850 nm) or five wavelengths (e.g., 690, 730, 770, 810, and 870 nm). A difference in light signal attenuation ("ΔA"—shown along the Y-axis of the graph) was calculated from the near ($N_\lambda$) and far ($F_\lambda$) detectors for each wavelength on the sensor combined: $\Delta A = -\text{Log } 10\ [(F_{\lambda_n}/N_{\lambda_n})/(F_{\lambda_{810}}/N_{\lambda_{810}})]$, whereas the 810 nm wavelength was used as a reference wavelength to normalize all subject data.

The dashed line 32 shown in FIG. 3 divides data that illustrates excessive absorption of light at certain wavelengths used in the NIRS interrogation (i.e., data points above the dashed line 32) from data that illustrates normal absorption of light at the same wavelengths (i.e., data points below the dashed line 32). The dashed line 32 shown in FIG. 3 also provides a dividing line for oximeter performance. Specifically, our experience is that conventional cerebral oximeters typically have the ability to calculate a tissue oxygen saturation value (StO2) from the data below the line with a reasonable degree of accuracy; e.g., data from control subjects having normal tissue optical properties, without any excessive absorption of certain wavelengths of light used in NIRS interrogation. Our experience is also that conventional cerebral oximeters typically do not have the ability to calculate a tissue oxygen saturation value (StO2) from the data above the dashed line 32 with a reasonable degree of accuracy, or at all; e.g., data from control subjects having tissue optical properties that result in an excessive absorption of certain wavelengths of light used in NIRS interrogation.

Figure 7:
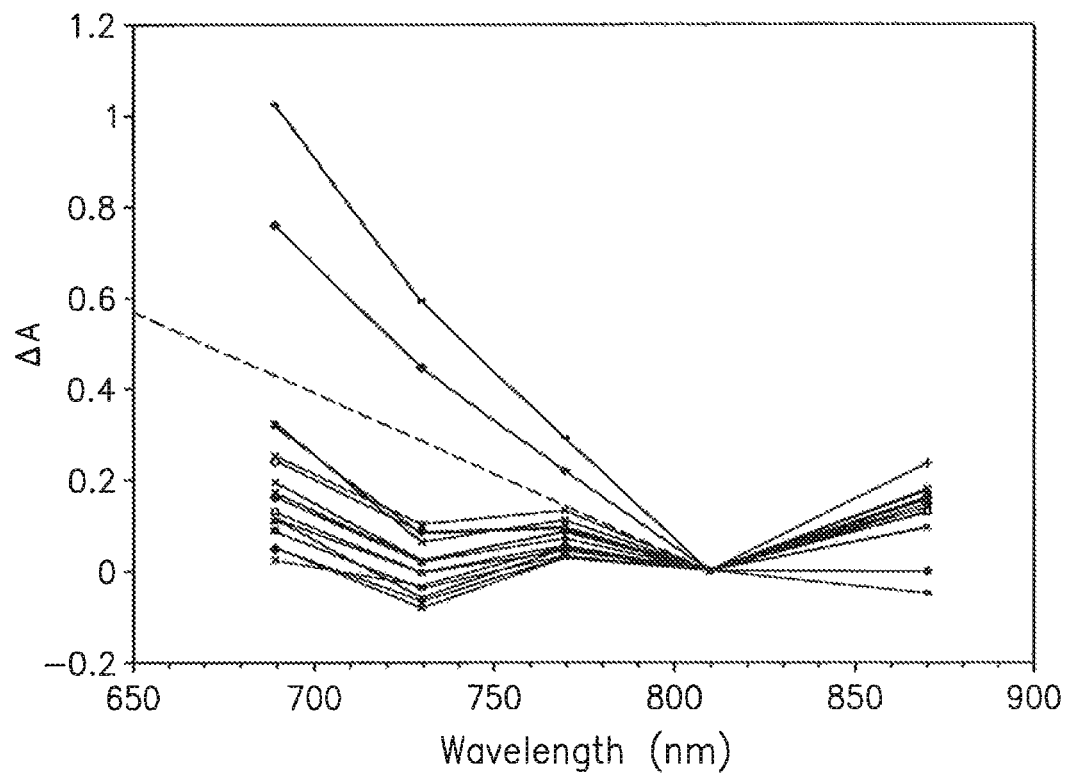
FIG. 7 is a graph illustrating a difference in attenuation versus wavelength, including data attributable to tissue exhibiting excessive absorption.

According to aspects of the present disclosure, the processing portion 12 is adapted to examine wavelengths lower than 810 nm, which is near the hemoglobin isosbestic point where the light absorption of oxyhemoglobin and deoxyhemoglobin are about the same. The processing portion 12 may be adapted according to several embodiments (described below) to use one or more discrete examining wavelengths to facilitate identification and differentiation of subject tissue having optical properties that exhibit excessive absorption of light from subject tissue having normal/expected tissue optical properties. FIG. 7 shows data from a five wavelength NIRS oximeter system whereas four of the wavelengths are 810 nm and lower. The data shown in FIG. 7 was collected from a Fore-Sight® NIRS sensor placed on the subject's forehead. Data collected was from five wavelengths (690 nm, 730 nm, 770 nm, 810 nm, and 870 nm). The difference in light signal attenuation (ΔA—shown along the Y-axis) was calculated from the near ($N_\lambda$) and far ($F_\lambda$) detectors for each wavelength on the sensor combined: $\Delta A = -\text{Log } 10\ [(F_{\lambda_n}/N_{\lambda_n})/(F_{\lambda_{810}}/N_{\lambda_{810}})]$ whereas the 810 nm wavelength was used as a reference wavelength to normalize all subject data.

In the following embodiments of the present disclosure, a method for non-invasively determining a blood oxygen parameter value of a subject's tissue is provided. In these embodiments, a spectrophotometric sensor is provided that includes the processing portion 12 and at least one transducer 10. The transducer 10 is operable to transmit light (e.g., incident light produced by a light source 18) at predetermined wavelengths into the subject's tissue. The transducer is further operable to detect (e.g., using light detectors 19, 20) at least a portion of the transmitted light after passage through the subject's tissue and to produce initial signal data from the light sensed. The term "initial signal data" as used herein refers to electronic signals of a type that enable the intensity of the light signal sensed by the light detectors to be quantified for the determination of attenuation of the incident light at the predetermined wavelengths after that light has passed through the subject's tissue. The term "initial signal data" also is used herein to refer to signal data produced by the transducer 10 that may be used to determine the presence of tissue optical properties associated with excessive absorption of such light. The initial signal data may be produced once and relied upon throughout a period of time in which the non-invasive testing is performed continuously on a particular tissue area. Alternatively, the initial signal data may be produced periodically throughout a period of time in which the non-invasive testing is performed continuously on a particular tissue area; e.g., the period of time in which the non-invasive testing is performed continuously (i.e., the total period) may be considered in terms of sub-periods of the total period, and an initial signal data set produced and used for each sub-period.

Figure 8:
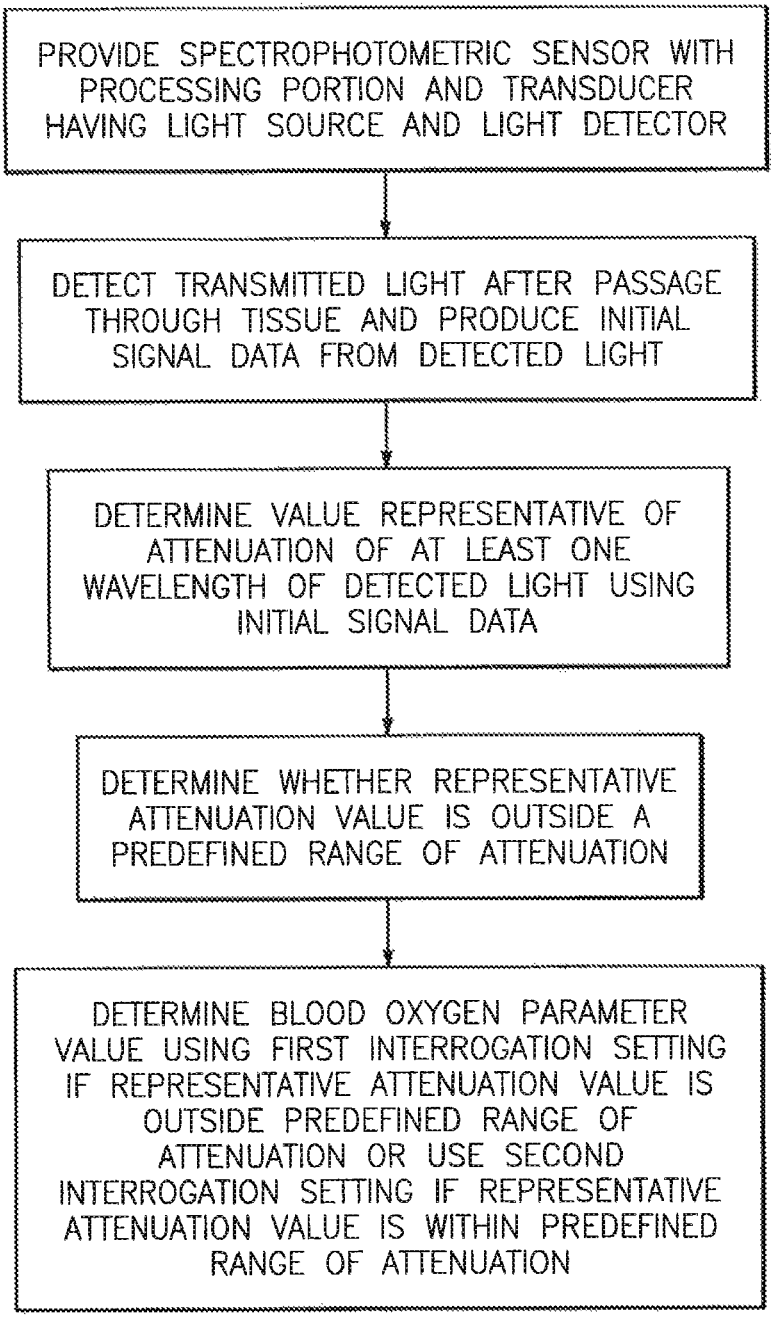
FIG. 8 is a flow chart illustrating steps according to an aspect of the present disclosure.

According to a first embodiment of the present disclosure (see flow chart of FIG. 8), the processing portion may be adapted to: a) determine a value representative of an attenuation of at least one of the predetermined wavelengths of light detected using the initial signal data; b) determine whether the representative attenuation value is outside (e.g., greater) a predefined range of attenuation values; and c) determine the blood oxygen parameter value using a first interrogation setting if the representative attenuation value is outside the predefined range of attenuation values, or using a second interrogation setting if the representative attenuation value is within the predefined range of attenuation values.

In this embodiment, the value representative of an attenuation of at least one of the predetermined wavelengths of light (i.e., the "representative attenuation value") detected using the initial signal data may be determined using a known intensity of incident light at the predetermined wavelength of light (i.e., the light entering the tissue) and the sensed intensity of the light sensed at the predetermined wavelength of light (i.e., the sensed light that has traveled through the subject's tissue). As indicated above, a variety of techniques (typically using a variant of the Beer-Lambert law) can be used to account for the attenuation at the light at the predetermined wavelength. FIGS. 3 and 7, for example, illustrate attenuation values in terms of "ΔA" which is an attenuation value normalized using absorption values detected at the 810 nm wavelength. The present disclosure is not limited to any particular expression of an attenuation value.

The term "predefined range of attenuation values" as used in this embodiment refers to a range of attenuation values that are associated with "normal" subjects (e.g., representing the majority of patient populations). As indicated above, "normal" subjects are those subjects having tissue optical properties with a light absorption value that is within predictable range for the specific test/data format parameters. The specific range may be chosen in a variety of different ways; e.g., the range may be a numerical value range based on empirical data, or may be chosen from a database of empirical values, etc. In addition, the term "range" as used herein, contemplates not only a spread of values between a first value and a second value, which spread may include the specific first value and the second value, but also contemplates a threshold value (e.g., a single value range). If within the present disclosure, therefore, it is described that a value is "outside of a predefined range", then the present disclosure contemplates that the range may be a threshold value to which another value may be compared; e.g., a comparison or determination of whether a particular value is above or below the threshold value.

The step of determining a blood oxygen parameter value recited within this embodiment recites a "first interrogation setting" and a "second interrogation setting". The term "interrogation setting" refers to a parameter in the determination of the blood oxygen parameter value. For example, the processing portion 12 may be adapted to use a particular set of wavelengths when determining the blood oxygen parameter value; e.g., a plurality of wavelengths in the range of 600 nm to 900 nm. Testing indicates that the certain wavelengths (e.g., 690 nm, 770 nm, 810 nm, and 870 nm) are particularly useful for producing accurate attenuation values when normal subjects are tested. Testing further indicates that attenuation values determined at lower wavelengths (e.g., between 600 nm and 720 nm) for subject tissue having tissue optical properties associated with excessive absorption are of limited value (or are unusable) due to excessive light absorption by the tissue relative to light absorption by hemoglobin. Hence, the light absorption at these wavelengths is predominated by the tissue rather than the blood component and as a result the signal-to-noise ratio compromises the attenuation values. If the attenuation contribution attributable to the tissue is not recognized (as is typical using conventional oximeter devices), erroneous data may be determined. According to this aspect of the present disclosure, if the representative attenuation value is outside (e.g., greater than) the predefined range of attenuation values then a "first interrogation setting" in the form of a set of wavelengths that does not include a wavelength(s) compromised by the attenuation attributable to the tissue is used to determine the blood oxygen parameter value; e.g., the "first interrogation setting" may be a set of wavelengths that does not include a wavelength in the range of 600-720 nm. On the other hand, if the representative attenuation value is within the predefined range of attenuation values then a "second interrogation setting" in the form of a set of wavelengths that includes a wavelength(s) in the range of 600-720 nm may be used to determine the blood parameter value, since wavelengths in this range are not compromised by the tissue optical properties of a normal subject.

In some embodiments, the set of wavelengths in the first interrogation setting may be shifted to higher wavelength values relative to the set of wavelengths within the second interrogation setting; e.g., the lowest wavelength of light within the first interrogation setting may be greater than the lowest wavelength of light in the second interrogation setting.

In an alternative embodiment, the first interrogation setting may be a value representative of the output of the light source (e.g., the intensity) within acceptable safety guidelines. In this alternative embodiment, if the representative attenuation value is greater than the predefined range of attenuation values (possibly by the ratio of incident light intensity to detected light intensity) then a "first interrogation setting" in the form of a first output value may be used. On the other hand, if the representative attenuation value is within the predefined range of attenuation values then a "second interrogation setting" in the form of a second output value, which second value is less than the first value, may be used. The greater first interrogation setting (i.e., output) will produce wavelengths of light at a greater intensity than will be produced by the lesser second interrogation setting, which greater intensity values will improve the signal-to-noise ratio at those wavelengths. There are, however, safety limitations regarding the level of light source output. The above embodiments are not limited by such safety considerations.

The above described first and second interrogation settings represent examples of interrogation settings and the present disclosure is not limited to these examples. Other interrogation settings may include calibration values, adjustment factors, etc. Furthermore, a plurality of interrogation settings can be employed with some combination thereof (e.g. weighted average or median) used to determine the value based upon the characteristics of the sensed data.

Figure 9:
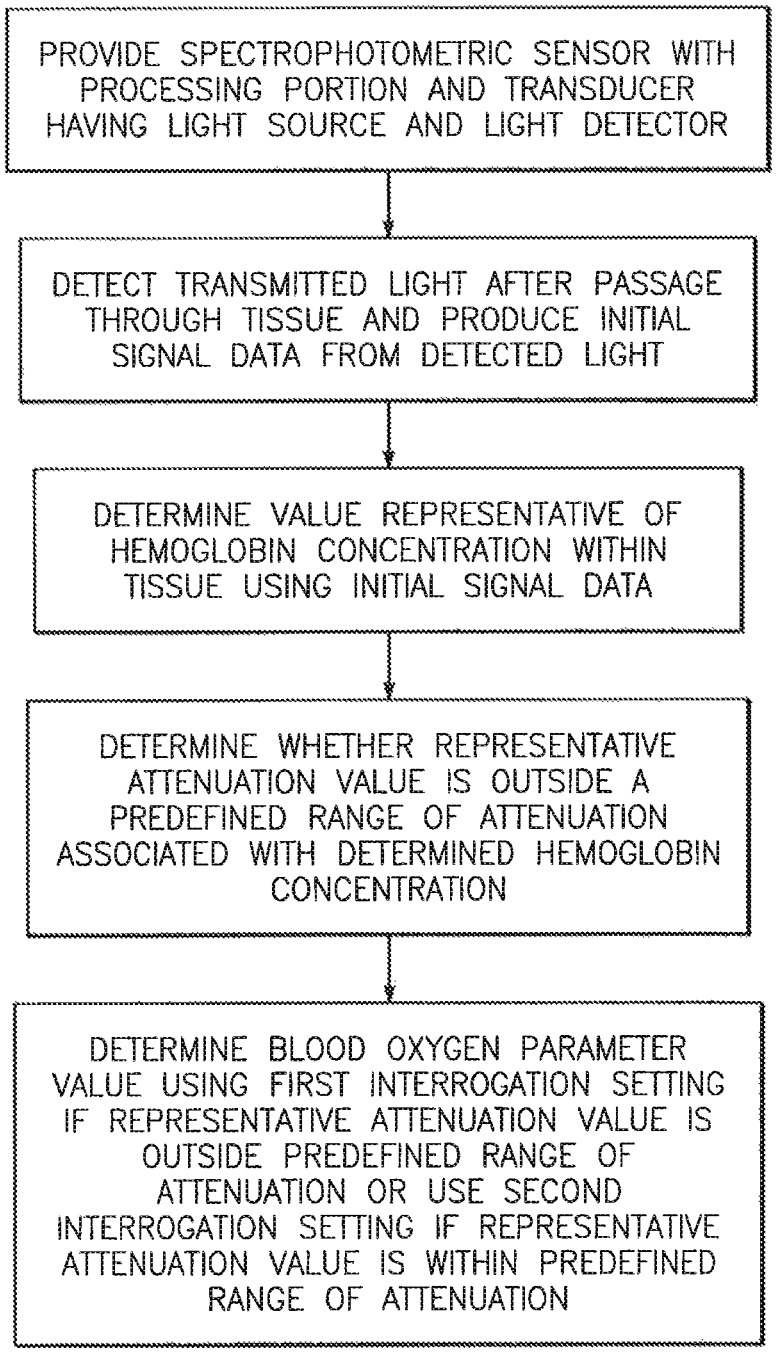
FIG. 9 is a flow chart illustrating steps according to an aspect of the present disclosure.

According to another embodiment of the present disclosure (see flow chart of FIG. 9), the processing portion may be adapted to: a) determine a value representative of an attenuation of at least one of the predetermined wavelengths of light detected using the initial signal data; b) determine a value representative of a hemoglobin concentration within the tissue; c) determine whether the representative attenuation value is greater than a predefined range of attenuation values associated with the determined hemoglobin concentration; and d) determine the blood oxygen parameter value using a first interrogation setting if the representative attenuation value is outside (e.g., greater than) the predefined range of attenuation values associated with the determined hemoglobin concentration, or using a second interrogation setting if the representative attenuation value is within the predefined range of attenuation values associated with the determined hemoglobin concentration.

The term "hemoglobin concentration" value as used in this embodiment refers to a determined value of a type of hemoglobin; e.g., oxyhemoglobin (HbO2), or deoxyhemoglobin (Hb) value, or both. Methods and techniques for determining a hemoglobin concentration value are known in the art; e.g., see U.S. Pat. Nos. 6,456,862; 7,072,701; and 8,396,526, all of which are identified and incorporated by reference above. The present disclosure is not limited to these described methods for determining a hemoglobin concentration value, and is also not limited to using HbO2 and/or Hb type hemoglobin values.

The "predefined range of attenuation associated with the determined hemoglobin concentration" as recited in this embodiment refers to a range of attenuation values that are associated with a particular hemoglobin concentration value. The range of attenuation values associated with a chosen hemoglobin concentration(s) (e.g., HbO2) may be based on attenuation values associated with hemoglobin concentration values (e.g., HbO2) determined within a statistically acceptable population of "normal" subjects as described above. The specific range may be chosen in a variety of different ways; e.g., the range may be a numerical value range based on empirical data, or may be chosen from a database of empirical values, etc.

In a manner similar to that described in the above embodiment, if the determined attenuation value is outside (e.g., greater than) the predefined range of attenuation values associated with the determined hemoglobin concentration value, then the first interrogation setting (e.g., a first set of wavelengths) may be used to determine the blood oxygen parameter value. On the other hand, if the determined attenuation value is within the predefined range of attenuation values associated with the determined hemoglobin concentration value, then the second interrogation setting (e.g., a second set of wavelengths) may be used to determine the blood oxygen parameter value.

Figure 10:
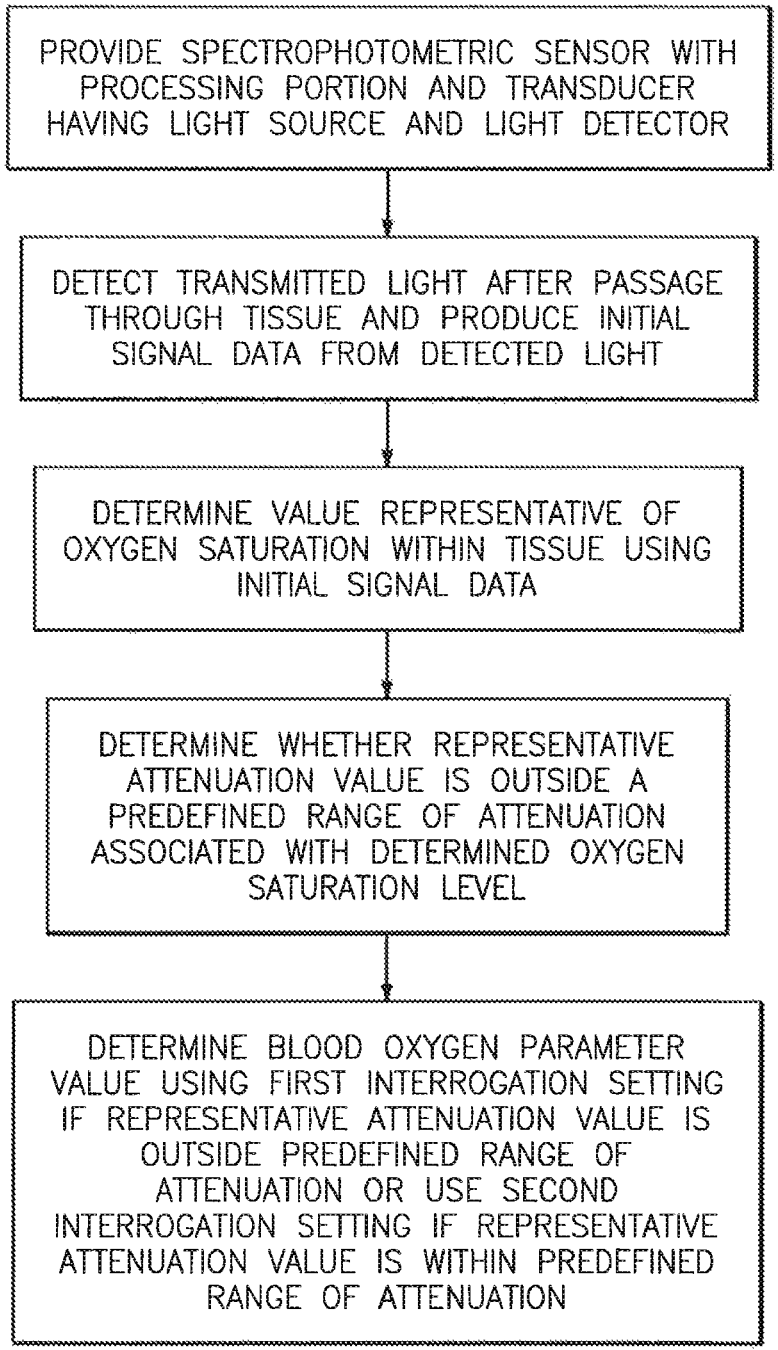
FIG. 10 is a flow chart illustrating steps according to an aspect of the present disclosure.

According to another embodiment of the present disclosure (see flow chart of FIG. 10), the processing portion 12 may be adapted to: a) determine a value representative of an attenuation of at least one of the predetermined wavelengths of light detected using the initial signal data, b) determine a value representative of the oxygen saturation value of the tissue using the initial signal data; c) determine whether the representative attenuation value is greater than a predetermined range of attenuation values associated with the determined oxygen saturation value; and d) determine the blood oxygen parameter value using a first interrogation setting if the representative attenuation value is outside (e.g., greater than) the predefined range of attenuation values associated with the determined oxygen saturation value, or using a second interrogation setting if the representative attenuation value is within the predefined range of attenuation values associated with the determined oxygen saturation value.

Regarding the term "oxygen saturation value" as used in this embodiment, methods and techniques for determining an oxygen saturation value are known in the art; e.g., see U.S. Pat. Nos. 6,456,862; 7,072,701; and 8,396,526, all of which are identified and incorporated by reference above. The present disclosure is not limited to these described methods for determining an oxygen saturation value.

In a manner similar to that described in the above embodiment, if the determined attenuation value is greater than the predefined range of attenuation values associated with the determined oxygen saturation value, then the first interrogation setting (e.g., a first set of wavelengths) may be used to determine the blood oxygen parameter value. On the other hand, if the determined attenuation value is within the predefined range of attenuation values associated with the determined oxygen saturation value, then the second interrogation setting (e.g., a second set of wavelengths) may be used to determine the blood oxygen parameter value.

Figure 11:
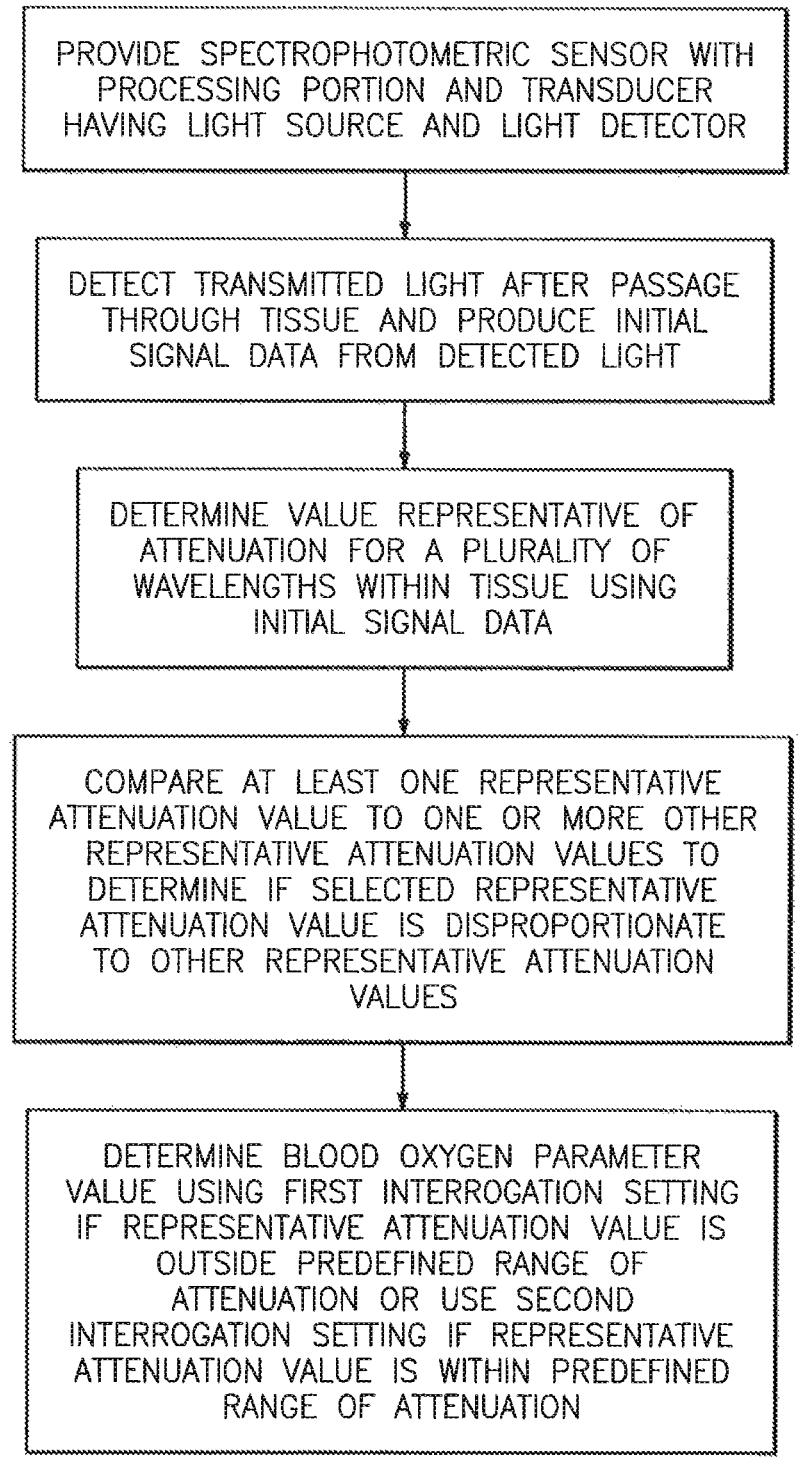
FIG. 11 is a flow chart illustrating steps according to an aspect of the present disclosure.

According to another embodiment of the present disclosure (see flow chart of FIG. 11), the processing portion 12 may be adapted to: a) determine a value representative of an attenuation for each of a plurality of the predetermined wavelengths of light detected using the initial signal data; b) compare at least one of the representative attenuation values relative to one or more of the other representative attenuation values to determine whether the selected representative attenuation value is disproportionate to the representative attenuation value of one or more of the other wavelengths; and c) determine the blood oxygen parameter value using a first interrogation setting if the representative attenuation value of one or more of the wavelengths is disproportionate to the representative attenuation value of another of the predetermined wavelengths, or using a second interrogation setting if the representative attenuation value of one or more of the wavelengths is not disproportionate to the representative attenuation value of another of the predetermined wavelengths.

The phrase "whether the representative attenuation value for any wavelength is disproportionate to the representative attenuation value of one or more of the other wavelengths" utilizes the facts that: a) attenuation values at particular wavelengths are predictable and repeatable for subjects having "normal" (as that term is defined above) tissue optical properties; and b) attenuation values at particular wavelengths for subjects having tissue optical properties that create excessive absorption disproportionately attenuate light at the aforesaid wavelengths. It can be seen from FIG. 3, for example, that within the attenuation values for normal subjects (i.e., below the dashed line 32) there is an increase in the attenuation values for wavelengths less than 730 nm. However, it can also be seen from FIG. 3, that the attenuation values for subjects having tissue optical properties that create excessive absorption (i.e., above the dashed line 32) for wavelengths less than 730 nm increase disproportionately relative to normal subjects; e.g., the slopes of substantially all the attenuation lines above the dashed line 32 have a greater slope than the attenuation lines below the dashed line 32. Hence, the disproportionate attenuation (e.g., as evidenced by line slope) may be used as an indicator of subject's having tissue optical properties associated with excessive absorption.

Since many changes and variations of the disclosed embodiment of the invention may be made without departing from the inventive concept, it is not intended to limit the invention otherwise than as required by the appended claims. For example, the present disclosure is described above in terms of sensing blood oxygenation within cerebral tissue, the present method and apparatus are not limited to cerebral applications and can be used to determine tissue blood oxygenation saturation within tissue found elsewhere within the subject's body.

What is claimed is:

1. A method for non-invasively determining a blood oxygen parameter value of a subject's tissue, comprising the steps of:
    providing a spectrophotometric sensor that includes a processing portion and at least one transducer, which transducer is operable to transmit light at a first plurality of wavelengths in a range of about 600 nm to about 900 nm into the subject's tissue, and to sense the transmitted light;
    detecting at least a portion of the transmitted light after passage through the subject's tissue using the transducer, and producing initial signal data from the light sensed;
    using the processing portion to execute instructions stored in a memory device, which instructions cause the processing portion to:
        determine a value representative of an intensity attenuation of at least one wavelength of light within the first plurality of wavelengths that is less than about 720 nm using the initial signal data; and
        determine whether the representative intensity attenuation value is outside a predefined range of attenuation values; and
        determine the blood oxygen parameter value using a subset of the first plurality of predetermined wavelengths, which subset consists of a second plurality of wavelengths in a range of about 720 nm to about 900 nm, if the representative intensity attenuation value is outside the predefined range of attenuation values, or using the first plurality of wavelengths if the representative intensity attenuation value is within the predefined range of attenuation values.

2. A method for non-invasively determining a blood oxygen parameter value of a subject's tissue, comprising the steps of:
    providing a spectrophotometric sensor that includes a processing portion and at least one transducer, which transducer is operable to transmit light at a first plurality of wavelengths in a range of about 600 nm to about 900 nm into the subject's tissue, and to sense the transmitted light;

detecting at least a portion of the transmitted light after passage through the subject's tissue using the transducer, and producing initial signal data from the light sensed;

using the processing portion to execute instructions stored in a memory device, which instructions cause the processing portion to:

determine a first value representative of an intensity attenuation of at least one wavelength of light within the first plurality of wavelengths that is less than about 720 nm using the initial signal data;

determine a second value representative of an intensity attenuation of at least one wavelength of light within the first plurality of wavelengths that is greater than about 720 nm using the initial signal data;

determine if the first value representative of said intensity attenuation of at least one wavelength of light within the first plurality of wavelengths that is less than about 720 nm is disproportionate to the second value representative of said intensity attenuation of at least one wavelength of light within the first plurality of wavelengths that is greater than about 720 nm;

determine the blood oxygen parameter value using a subset of the first plurality of predetermined wavelengths, which subset consists of a second plurality of wavelengths in a range of about 720 nm to about 900 nm, if the first value is disproportionate to the second value, or using the first plurality of wavelengths if the first value is proportionate to the second value.

3. The method of claim 2, wherein the method is performed over a period of time, and wherein the initial signal data is produced once during the period of time.

4. The method of claim 2, wherein the method is performed over a period of time, and wherein the initial signal data is produced more than once during the period of time.

5. The method of claim 4, wherein the initial signal data is produced periodically during the period of time.

6. The method of claim 2, wherein a disproportionate first value relative to said second value is indicative of an altered tissue condition independent of the blood oxygen parameter value.

7. The method of claim 6, wherein the altered tissue condition includes one or more of a bruise, contusion, scarring, skull fracture, concussion, surgery scarring, infection, tissue discoloration, bone discoloration, dura pigmentation, bone marrow, or forehead hair follicles.

8. The method of claim 2, wherein said first value is disproportionate to said second value when the respective attenuations do not correspond to predetermined attenuation values.

9. The method of claim 8, wherein the predetermined attenuation values are representative of attenuation values determined using substantially the same spectrophotometric processes on a normal subject.

10. The method of claim 8, wherein the predetermined attenuation values are based on empirical data.

11. An apparatus for non-invasively determining a blood oxygen parameter value of a subject's tissue, comprising:

a spectrophotometric sensor that includes at least one processor and at least one transducer, which transducer is operable to transmit light at a first plurality of wavelengths in a range of about 600 nm to about 900 nm into the subject's tissue, and is operable to detect at least a portion of the transmitted light after passage through the subject's tissue, and to produce initial signal data representative of the light sensed;

wherein the at least one processor is in communication with a non-transitory memory storing instructions, which instructions when executed cause the processor to:

determine a first value representative of an intensity attenuation of at least one wavelength of light within the first plurality of wavelengths that is less than about 720 nm using the initial signal data;

determine a second value representative of an intensity attenuation of at least one wavelength of light within the first plurality of wavelengths that is greater than about 720 nm using the initial signal data;

determine if the first value representative of said intensity attenuation of at least one wavelength of light within the first plurality of wavelengths that is less than about 720 nm is disproportionate to the second value representative of said intensity attenuation of at least one wavelength of light within the first plurality of wavelengths that is greater than about 720 nm; and determine the blood oxygen parameter value using a subset of the first plurality of predetermined wavelengths, which subset consists of a second plurality of wavelengths in a range of about 720 nm to about 900 nm, if the first value is disproportionate to the second value, or using the first plurality of wavelengths if the first value is proportionate to the second value.

12. The apparatus of claim 11, wherein the instructions when executed cause the processor to produce the initial signal data periodically during a period of time.

13. The apparatus of claim 11, wherein a disproportionate first value relative to said second value is indicative of an altered tissue condition independent of the blood oxygen parameter value.

14. The apparatus of claim 13, wherein the altered tissue condition includes one or more of a bruise, contusion, scarring, skull fracture, concussion, surgery scarring, infection, tissue discoloration, bone discoloration, dura pigmentation, bone marrow, or forehead hair follicles.

* * * * *